United States Patent [19]
Gold

[11] Patent Number: 5,098,419
[45] Date of Patent: Mar. 24, 1992

[54] UNDERGARMENT TO BE WORN BY INCONTINENT PERSONS

[75] Inventor: David L. Gold, Mahwah, N.J.

[73] Assignee: Nantucket Industries, Incorporated, New York, N.Y.

[21] Appl. No.: 555,259

[22] Filed: Jul. 19, 1990

[51] Int. Cl.[5] .................. A61F 13/15; A41B 9/00; A41B 9/02
[52] U.S. Cl. .................. 604/396; 604/393; 2/401
[58] Field of Search ............... 604/393, 396, 397, 394; 2/400, 402

[56] References Cited

U.S. PATENT DOCUMENTS

| | | | |
|---|---|---|---|
| 4,044,769 | 8/1977 | Papajohn | 604/396 |
| 4,227,531 | 10/1980 | McLeod | 604/396 |
| 4,351,340 | 9/1982 | McLeod | 604/396 |
| 4,352,356 | 10/1982 | Tong | 604/393 |
| 4,490,856 | 1/1985 | Dost | 2/400 |
| 4,880,424 | 11/1989 | Rautenberg | 604/396 |
| 4,938,757 | 7/1990 | Van Gompel et al. | 604/396 |

*Primary Examiner*—David Isabella
*Assistant Examiner*—Elizabeth M. Burke
*Attorney, Agent, or Firm*—Wolf, Greenfield & Sacks

[57] ABSTRACT

An undergarment that retains urine and other body fluids comprises an upper, or body, portion made of a knitted fabric, and a lower, or crotch, portion made of a woven, non-woven or knitted fabric. The crotch portion is coated with a modified polyester urethane polymer which prevents passage of body fluids, yet allows for some of the body condensate to escape by moisture vapor transmission. Because the crotch material is coated, rather than laminated, the garment body and crotch portion can be assembled without using special sewing needles, methods or speeds.

12 Claims, 1 Drawing Sheet 5,098,419

UNDERGARMENT TO BE WORN BY INCONTINENT PERSONS

FIELD OF THE INVENTION

This invention relates to protective undergarments, and more particularly to undergarments which have a liquid resistant crotch, primarily for use by those who are affected by urinary incontinence.

BACKGROUND OF THE INVENTION

While incontinence may be caused by a wide variety of physical conditions, it is always sensitive and potentially embarrassing to someone affected by it. However, there are many conventional undergarments which are specifically made to allow the incontinent individual to function normally without constant worry about troublesome leakage of urine. These prior art garments, to one extent or another, treat the problem by retaining fluids and preventing accidents, but they typically suffer from several shortcomings, including a lack of user comfort, increased bulk causing the protective undergarment to be obvious beneath overgarments and high manufacturing costs due to the fact that special sewing needles, equipment, methods, and speeds are often necessary to handle the liquid resistant materials used to construct the garments.

Of primary importance in the design of an undergarment for those who suffer from incontinence is discreetness, so that the condition is not obvious. Discreetness is ensured by a garment which is unaudible, light-weight, soft and stretches so that it conforms to the user's body and is as similar to an ordinary undergarment as possible.

In general, it is also desirable that the liquid resistant crotch portion of the undergarment be durable, washable, water and stain resistant and odor free. Optimally, the crotch material should not become tacky, crack, peel or breakdown throughout repeated washings. It is also highly desirable that the crotch material, as well as the body fabric, "breathe", or transmit moisture vapor to some extent, in order to allow the user's body condensate to escape. Of course, moisture vapor transmission is not so extensive that other liquids, such as urine, are passed so that the garment cannot perform its intended function. This "breathable" characteristic allows an extra degree of comfort during use and avoids a clammy feeling. It is also necessary that the undergarment be adaptable for use with a disposable absorbent crotch pad, which is used for incontinence, and also during a woman's menstrual flow, to absorb liquids. In order to accomodate conventional pads, which have partial adhesive backings, the garment crotch material must allow easy removal of the pads for disposal without causing damage to the crotch material.

One conventional undergarment which possesses some of the above features is disclosed in U.S. Pat. 4,880,424. This latter undergarment is comprised of a knitted body material attached to a laminated crotch portion. The laminated portion, in turn, is comprised of a stretchable fabric backing, bonded with an adhesive, to a thermoplastic stretch film which is liquid proof. However, the two part garment construction requires careful fabrication techniques due to the fact that the laminated material used in the crotch portion must be sewn to the knitted body material. Accordingly, the patent disclosure necessitates the use of special threads, needles, equipment and sewing speeds to handle the laminated material. The special manufacturing requirements inevitably increase garment costs.

Accordingly, it is an object of the present invention to provide an undergarment for incontinent persons, which garment is comfortable and discreet.

It is another object of the present invention to provide an undergarment for incontinent persons, the crotch portion of which resists passage of urine and other body fluids, yet allows for some of the user's body condensate to escape by moisture vapor transmission.

It is still another object of the present invention to provide an undergarment for incontinent persons, which garment maintains its shape under repeated washings.

It is yet another object of the present invention to provide an undergarment for incontinent persons, which garment will accept disposable absorbent shields for incontinence and also for use during a woman's menstrual flow.

It is a further object of the present invention to provide an undergarment for incontinent persons, which garment has a body material and separate crotch portion constructed of a coated fabric.

It is yet a further object of the present invention to provide an undergarment for incontinent persons, which garment can be fabricated using standard sewing equipment, speeds and techniques.

SUMMARY OF THE INVENTION

The foregoing objects ar achieved and the foregoing problems are solved, in one illustrative embodiment of the present invention, in which an undergarment for incontinent persons comprises an upper, or body, portion made of a knitted fabric, and a lower, or crotch, portion made of a woven, non woven or knitted fabric. The crotch portion is coated with a modified polyester urethane polymer which prevents passage of body fluids, yet allows for some of the body condensate to escape by moisture vapor transmission. Because the crotch material is coated, rather than laminated, the garment body and crotch portions can be assembled without using special sewing needles, methods or speeds.

DETAILED DESCRIPTION OF THE PREFERRED EMBODIMENT

Figure 1:
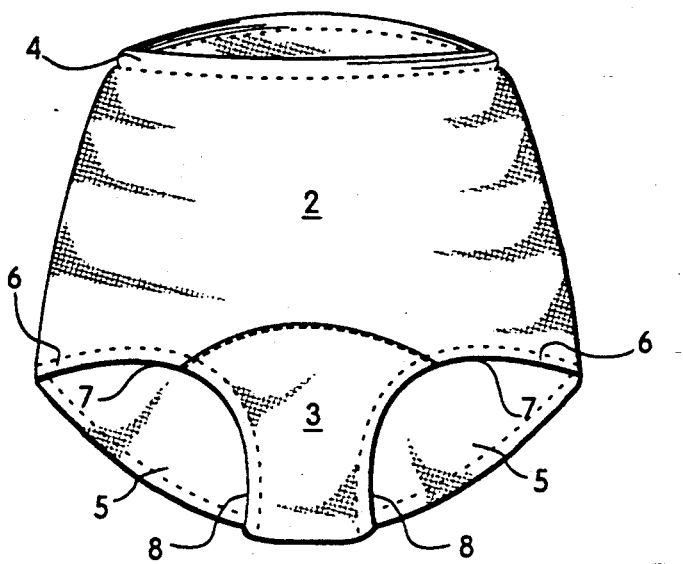
FIG. 1 is a front view of an undergarment constructed in accordance with the invention.
Figure 2:
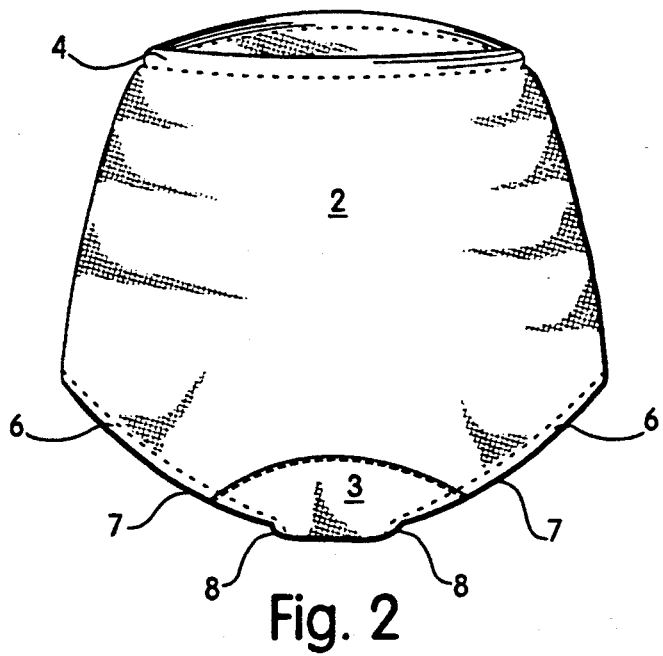
FIG. 2 is a rear view of the garment shown in FIG. 1.

FIGS. 1 and 2 show an undergarment constructed in accordance with the principles of the present invention. The garment consists of a body 2, which may be comprised wholly of natural or synthetic yarns or fibers in any combination or blend. The fabric may illustratively be a construction commonly considered as knitted, which has sufficient all around stretch to provide a comfortable fit to the user. Although many fabrics and blends can be used, two particular fabric blends have been found to be preferable. The first preferred fabric blend is approximately a 90/10 percent (fiber content) blend of cotton and LYCRA (LYCRA is a trademark of E. I. Du Pont De Nemours and Company for its stretchable spandex fiber). This material is lightweight and maintains air circulation around the user's body to prevent heat buildup. It has a soft, silky feel and is relatively stable, so that there is little shrinkage after repeated washings. The material also has all way stretch and good shape retention that allows a contoured fit without sags or bulges.

The second preferred material is approximately an 85/15 percent (fiber content) blend of SUPPLEX and LYCRA (SUPPLEX is a trademark of the E.I. Du Pont De Nemours and Company for a nylon yarn that contains finer, more numerous filaments). This latter material looks, feels and breathes like pure cotton, but is stronger, resists stains and fading, is lightweight and dries fast through a wicking action. There is minimal shrinkage after repeated washings. The material also has all way stretch and good shape retention that allows a contoured fit without sags or bulges. Of the two preferred fabrics, the cotton/LYCRA blend is currently substantially less expensive and thus further reduces the overall cost of the undergarment.

The body fabric is sewn into the upper portion of a conventional undergarment or panty shape having a shirred waistband 4 and an upper half 7 of legholes 5. Legholes 5 are illustratively provided with an encircling band of elastic shirring 6 so that they fit snugly against the wearer's thighs and prevent fluid leakage.

Figure 3:
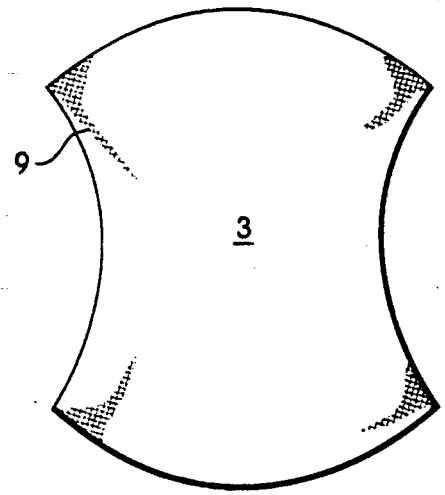
FIG. 3 is a top view of the crotch portion of the undergarment.

The illustrative undergarment in FIGS. 1 and 2 is also provided with a crotch portion 3, the shape of which is shown in more detail in FIG. 3. Crotch portion 3 illustratively consists of a light weight material 9 comprised of natural or synthetic fibers, or a combination or blend thereof, and is cut in an approximately "hourglass" shape to form the bottom of the garment. The sides 8 of the crotch portion form the bottom section 8 of legholes 5. The crotch fabric 9 may be comprised of woven, non-woven, or knitted material. In order for the material 9 to resist the passage of body fluids, it is coated with a modified polyester urethane polymer that is formulated in such a way that the material remains soft, light weight, durable, washable, waterproof, stain-resistant and odor free. Other conventional ingredients may be added to the coating material which render it hypo allergenic, non toxic, antimicrobial and antifungal.

One crotch fabric 9 which has been found to be particularly suitable is designated as INNOFAB 4400 IA, manufactured by Miltex International, Incorporated, 41 Brook Street, Manchester, N.H. 03104. This material is a woven 70 denier nylon fabric coated with a modified polyester urethane polymer formulation. Typical specifications for this material when used in the construction of undergarments are set forth in the following Table I

TABLE I

Weight: 2.3 oz./sq. yd.
Thickness: 0.005"
Water Resistance: 135 psi to burst when new
Sterilizability: Boilable in water to 212° F. with bleach or soil remover; autoclavable to 276° F. without fabric breakdown or loss of waterproofing
Durability: retains 100+ psi water resistance and shrinks less than 1% after approximately 100 washings The material is resistant to disinfectants such as bleach, caustic soil remover, phenol and quaternary ammonium (typical disinfectants used in hospitals) and, because the material is coated rather than laminated, the body portion and the crotch portion of the garment may be assembled together using standard needles, methods and sewing speeds.

Undergarments were constructed using the above-mentioned fabrics and including conventional antimicrobial and antifungal compounds in the coating mixture. The crotch portions of these garments were tested and the results are set forth in the following laboratory test report in Table II:

TABLE II

| ITEM | RESULTS |
| --- | --- |
| Mullen Hydrostat - Initial | 135 psi |
| Mullen Hydrostat after 10 min. wash in abrader w/boiling water | 125 psi |
| Mullen after 10 min. wash in abrader with boiling water + 8% bleach solutions | 130 psi |
| Mullen 10 min. wash in abrader with boiling water + 4% caustic solution | 115 psi |
| Disinfectant Test using Phenol and quaternary ammonium compound chemicals to determine durability | Passed-no appreciable loss in Mullens. Does not become tacky. |
| Antimicrobial AATCC Method 147-1982 *Staphylococcus Aureus* | Pass |
| Antifungal - AATCC Method 30-1987 *Aspergillus Niger* | Pass |

The inventive undergarment is designed for use with a conventional disposable, absorbent incontinent pad (not shown) or for use with a conventional, disposable menstrual flow pad (not shown). These pads typically comprise an absorbent layer with a partial adhesive backing that holds the pad in place within the undergarment. The coating on the material 9 of crotch portion 3 allows the adhesive backing of the pads to grip the crotch portion, yet enables the pad to be easily removed from the undergarment without damaging the crotch material. In use, the absorbent pad lies between the garment crotch portion and the wearer's body and absorbs body fluids.

Although only one illustrative embodiment has been shown in the inventive undergarment, other modifications and changes will be immediately apparent to those skilled in the art. These modifications and changes are intended to be covered by the following claims.

What is claimed is:

1. An undergarment for use by incontinent persons, said garment having a waistband and leg holes and comprising:
    a body portion shaped so as to be worn around the central portion of a wearer's body, said body portion being constructed of knitted fabric and having a shirred waistband and an open bottom with shirred partial leg holes; and
    a substantially inelastic crotch portion consisting essentially of a single layer of material impregnated with a modified polyester urethane polymer to resist the passage of liquids therethrough, said crotch portion being sewn to said body portion to complete said leg holes and said undergarment.

2. An undergarment according to claim 1 wherein said knitted body fabric is an approximately 90/10 percent fiber content blend of cotton and LYCRA material.

3. An undergarment according to claim 1 wherein said knitted body fabric is an approximately 85/15 percent fiber content blend of SUPPLEX and LYCRA material.

4. An undergarment according to claim 1 wherein said crotch material is a coated, woven material.

5. An undergarment according to claim 1 wherein said crotch material is a coated, non-woven material.

6. An undergarment according to claim 1 wherein said crotch material is a coated, knitted material.

7. An undergarment according to claim 1 wherein said crotch material si a coated, woven nylon material.

8. An undergarment according to claim 1 wherein said crotch material is INNOFAB 4400-IA material.

9. An undergarment for use by incontinent persons, said garment having a waistband and leg holes and comprising:
   a body portion shaped so as to be worn around the central portion of a wearer's body, said body portion being constructed entirely of a knitted fabric blend and having a shirred waistband and an open bottom with shirred partial leg holes; and
   a substantially inelastic crotch portion consisting essentially of a single layer of light-weight woven nylon material impregnated with a modified polyester urethane polymer to resist the passage of liquids therethrough, said crotch portion having an approximate hourglass shape and being sewn to said body portion to complete said legholes and said under garment.

10. An undergarment according to claim 9 wherein said knitted body fabric blend is an approximately 90/10 percent fiber content blend of cotton and LYCRA material.

11. An undergarment according to claim 9 wherein said knitted body fabric blend is an approximately 85/15 percent fiber content blend of SUPPLEX and LYCRA material.

12. An undergarment according to claim 9 wherein said crotch material is INNOFAB 4400 IA material.

* * * * *